(12) United States Patent
Sklansky et al.

(10) Patent No.: US 8,923,477 B2
(45) Date of Patent: *Dec. 30, 2014

(54) FIDUCIAL SYSTEMS FOR MAMMOGRAPHY

(71) Applicant: Image Mining, Inc., Corona del Mar, CA (US)

(72) Inventors: Jack Sklansky, Corona del Mar, CA (US); Jeffrey Klein, Newport Beach, CA (US)

(73) Assignee: Image Mining, Inc., Corona Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/967,215

(22) Filed: Aug. 14, 2013

(65) Prior Publication Data

US 2014/0029718 A1 Jan. 30, 2014

Related U.S. Application Data

(63) Continuation of application No. 13/161,329, filed on Jun. 15, 2011, now Pat. No. 8,515,006.

(60) Provisional application No. 61/355,074, filed on Jun. 15, 2010.

(51) Int. Cl.
| | |
|---|---|
| *G01N 23/04* | (2006.01) |
| *A61B 6/00* | (2006.01) |
| *A61B 6/04* | (2006.01) |
| *G06T 7/00* | (2006.01) |
| *A61B 19/00* | (2006.01) |

(52) U.S. Cl.
CPC ............ *A61B 6/0492* (2013.01); *A61B 6/4266* (2013.01); *A61B 2019/5437* (2013.01); *A61B 6/0414* (2013.01); *G06T 2207/10116* (2013.01); *G06T 2207/30068* (2013.01); *A61B 6/502* (2013.01); *G06T 7/0028* (2013.01); *A61B 2019/5466* (2013.01); *A61B 6/5235* (2013.01); *G06T 2207/30204* (2013.01); *A61B 2019/5408* (2013.01)
USPC .............................................. 378/37; 378/205

(58) Field of Classification Search
USPC .............................. 378/37, 163, 205, 206, 207
See application file for complete search history.

(56) References Cited

U.S. PATENT DOCUMENTS 6,814,760 B2   11/2004   Anderson et al.
8,515,006 B2 *  8/2013   Sklansky et al. ................ 378/37
(Continued)

OTHER PUBLICATIONS

Richard O. Duda, et al., Pattern Classification, Second Edition, John Wiley & Sons, New York, 2001, Section 10.8, pp. 548-550.

(Continued)

*Primary Examiner* — Hoon Song
(74) *Attorney, Agent, or Firm* — James W. Hill; Nathan Smith McDermott Will & Emery LLP

(57) ABSTRACT

A system is described for breast imaging that includes spatially registering sequential mammographic images of the same breast. The system includes a first compression member configured to contact a first side of a breast, a second compression member configured to contact a second side of a breast that is substantially opposite the first side. The system further includes a first image sensor, coupled to the first compression member and configured to detect a position of a first fiducial marker located at the first side of the breast, and a second image sensor, coupled to the second compression member and configured to detect a position of a second fiducial marker located at the second side of the breast.

23 Claims, 15 Drawing Sheets

(56) References Cited

U.S. PATENT DOCUMENTS

| | | | |
|---|---|---|---|
| 2002/0188194 A1* | 12/2002 | Cosman | 600/426 |
| 2003/0167004 A1 | 9/2003 | Dines et al. | |
| 2006/0241406 A1 | 10/2006 | Noujeim | |
| 2007/0276229 A1 | 11/2007 | Adler | |
| 2008/0249415 A1 | 10/2008 | Okamura et al. | |
| 2008/0279330 A1* | 11/2008 | Ueki | 378/63 |

OTHER PUBLICATIONS

Kenichi Kanatani, et al., "Performance evaluation of iterative geometric fitting algorithms", Computational Statistics & Data Analysis, vol. 52, Issue 2, Oct. 2007, pp. 1208-1222.

* cited by examiner

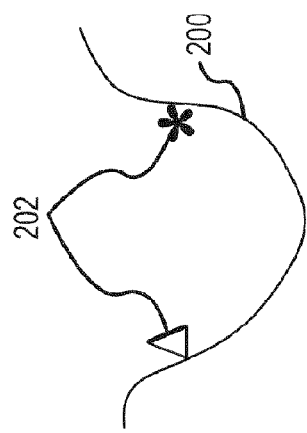
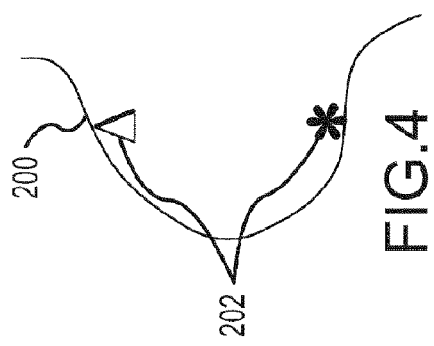
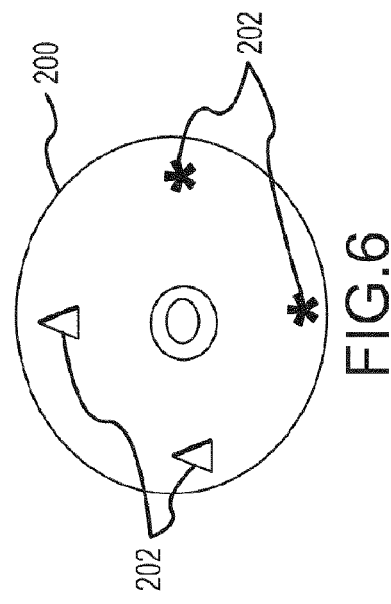

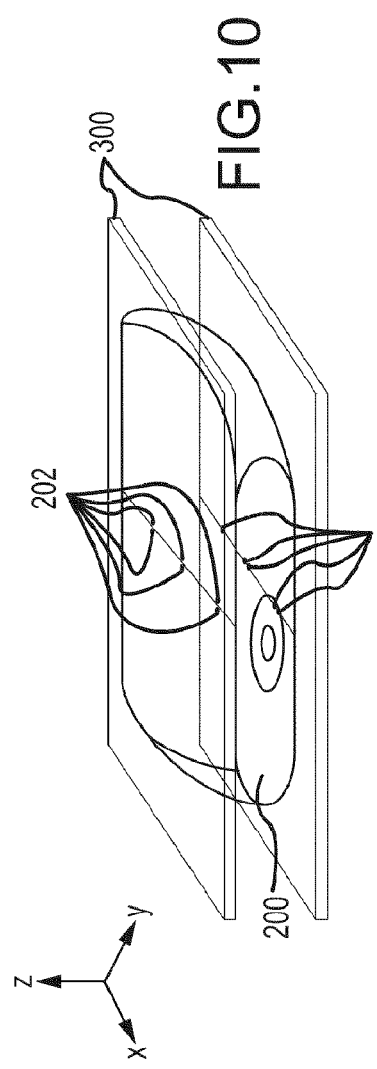
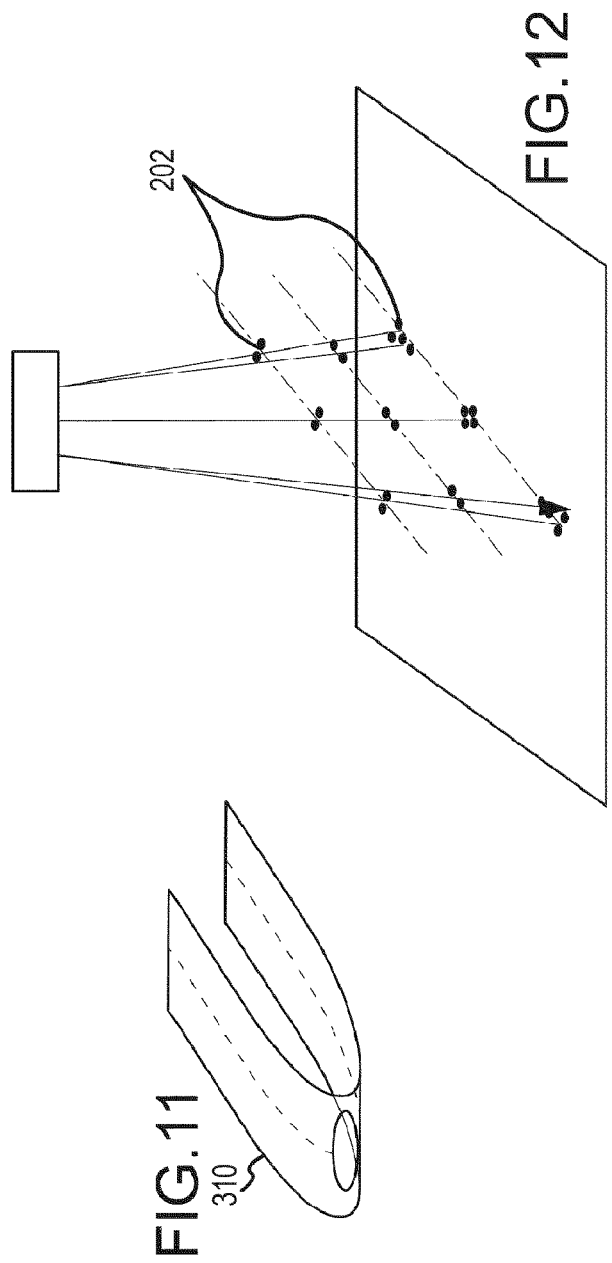

FIDUCIAL SYSTEMS FOR MAMMOGRAPHY

RELATED APPLICATION

This application is a continuation of U.S. patent application Ser. No. 13/161,329, filed Jun. 15, 2011, which claims priority benefit of U.S. Provisional Application No. 61/355,074, filed Jun. 15, 2010, the entireties of which are incorporated herein by reference.

FIELD

The subject technology generally relates to mammography and, more particularly, to spatially registering sequential mammographic images of the same breast.

BACKGROUND

Annual screening of mammograms is a medically recommended procedure for early detection of breast cancer in, for example, women 40 years of age or older. Unfortunately, this procedure can be subject to false positives and some missed cancers, especially among premenopausal women.

SUMMARY

The subject technology focuses on mammography, but is not restricted to that application. In mammography, the subject technology involves spatial registration of sequential images of the same breast. In a proper registration of two mammograms, deviations of the pixel values at corresponding positions in the two mammograms will signify a growth, damage or diseased tissue in the breast at that position.

A "fiducial marker" in the subject technology is any natural or artificially implanted object or stain in the breast tissue that can provide a reference point where the two successive mammograms can be made to coincide with high precision. A small tattoo on the skin or a recognizable punctate calcification are examples of possible fiducial markers.

In one embodiment of the subject disclosure, a system for breast imaging may comprise a first compression member, a second compression member, a first image sensor, a second image sensor and an alignment system. The first compression member may be configured to contact a first side of a breast. The second compression member may be configured to contact a second side of a breast that is substantially opposite the first side. The first image sensor may be coupled to the first compression member and may be configured to detect a position of a first fiducial marker located at the first side of the breast. The second image sensor may be coupled to the second compression member and configured to detect a position of a second fiducial marker located at the second side of the breast. The alignment system may receive information from at least one of the first and second image sensors and, based on the information, facilitate an alignment of the first and second fiducial markers.

In some embodiments, the system further comprises a positioner that, based on the information, moves at least one of the first and second compression members such that the breast is moved to align the first and second fiducial markers.

In some embodiments, the system further comprises the first fiducial marker, wherein the first fiducial marker is configured to be placed within about 1 cm of a skin surface at the first side of the breast.

In some embodiments, the system further comprises the second fiducial marker, wherein the second fiducial marker is configured to be placed within about 1 cm of a skin surface at the second side of the breast, different than the first side.

In some embodiments, the first compression member comprises a paddle.

In some embodiments, the first and second fiducial markers comprise one or more tattoos.

In some embodiments, the first and second fiducial markers are not visible to the natural eye.

In some embodiments, the first and second fiducial markers are visible to the natural eye when subject to ultra-violet illumination.

In some embodiments, the first and second fiducial markers are radiopaque.

In some embodiments, the alignment system comprises imaging software configured to further facilitate alignment of the first and second fiducial markers.

In some embodiments, the system further comprises an electromagnetic radiation system to generate electromagnetic radiation to facilitate generation of an image of the breast.

In some embodiments, the electromagnetic radiation comprises x-rays.

In some embodiments, the system further comprises at least a first radiographic image acquisition platform configured to acquire a first radiographic image of the breast at an initial time.

In some embodiments, the system further comprises a second radiographic image acquisition platform configured to acquire a second radiographic image of the breast at a subsequent time from the initial time.

In some embodiments, the system further comprises a subtraction radiography system configured to subtract the first radiographic image from the second radiographic image to facilitate detection of radiographic changes in the breast that have occurred between the initial time and the subsequent time.

Some embodiments include a method for breast imaging comprising the steps of contacting a first side of a breast with a first compression member and contacting a second side of a breast that is substantially opposite the first side with a second compression member. The method further comprises the steps of detecting a position of a first fiducial marker located at the first side of the breast with a first image sensor, coupled to the first compression member and detecting a position of a second fiducial marker located at the second side of the breast with a second image sensor, coupled to the second compression member. The method further comprises the steps of aligning information at an alignment system from at least one of the first and second image sensors and based on the acquired information, aligning the first and second fiducial markers.

In some embodiments, the aligning comprises moving at least one of the first and second compression members such that the breast is moved to align the fiducial markers based on the information received.

In some embodiments, the method further comprises the step of placing the first fiducial marker within about 1 cm of a skin surface at the first side of the breast.

In some embodiments, the method further comprises the step of placing the second fiducial marker within about 1 cm of a skin surface at the second side of the breast.

In some embodiments, the method further comprises the step of aligning the first and second fiducial markers with imaging software.

In some embodiments, the method further comprises the step of, generating electromagnetic radiation to generate a radiographic image of the breast.

In some embodiments, the method further comprises the step of acquiring a first image of the breast at an initial time.

In some embodiments, the method further comprises the step of acquiring a second image of the breast at a subsequent time from the initial time.

In some embodiments, the method further comprises the step of subtracting the first image from the second image to detect changes in the breast that have occurred between the initial time and the subsequent time.

It is understood that other embodiments of the subject technology will become readily apparent to those skilled in the art from the following detailed description, wherein various embodiments of the subject technology are shown and described by way of illustration. As will be realized, the subject technology is capable of other and different embodiments and its several details are capable of modification in various other respects, all without departing from the scope of the subject technology.

Accordingly, the drawings and detailed description are to be regarded as illustrative in nature and not as restrictive.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 4, 5 and 6 are exemplary images illustrating locations of pairs of opposing invisible tattoos in a patient's breast.

FIG. 10 illustrates an example of a breast compressed between two plates translucent to ultraviolet light.

FIG. 11 illustrates an example of a flexible clear plastic alignment with straight edge configured to facilitate precise alignment of the breast.

FIG. 12 illustrates exemplary x-ray images of two linear arrays of tattooed dots projected onto an x-ray sensitive plate, where adjacent dot-pairs are equidistant apart.

DETAILED DESCRIPTION

The detailed description set forth below is intended as a description of various embodiments of the subject technology and is not intended to represent the only embodiments in which the subject technology may be practiced. The appended drawings are incorporated herein and constitute a part of the detailed description. The detailed description includes specific details for providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like or similar components may be labeled with identical element numbers for ease of understanding or it may indicated in the disclosure that one component may be an example of a different component.

Embodiments of the subject technology may be designed to overcome the errors in screening premenopausal women, for example, and in particular to reduce the number of false positives.

Figure 1:
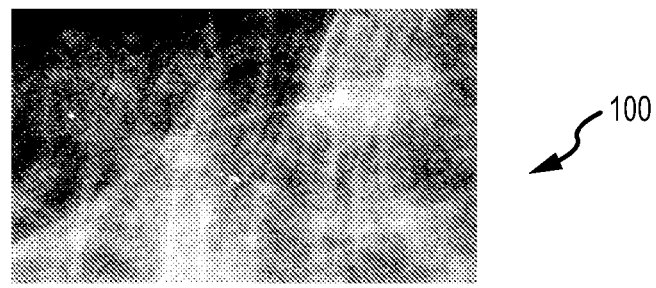
FIG. 1 is a diagram illustrating an example of an initial mammogram ("Mammo 0") at time t=0.
Figure 2:
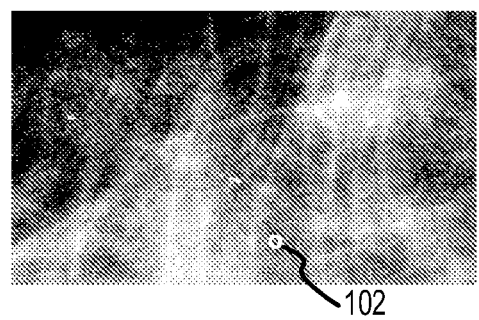
FIG. 2 is a diagram illustrating an example of a subsequent mammogram ("Mammo T") at time t=T.
Figure 3:
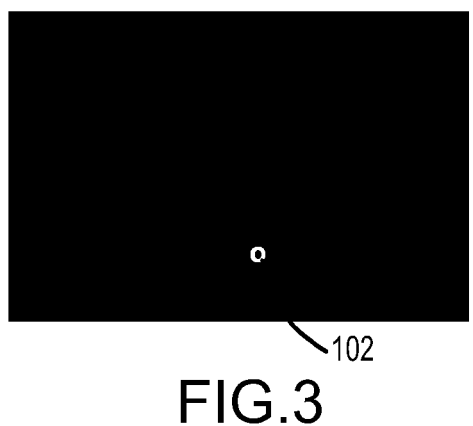
FIG. 3 is a diagram illustrating an example of the subtraction of Mammo 0 of FIG. 1 from Mammo T of FIG. 2.

In some embodiments, two mammograms of a breast, each mammogram produced in exactly the same breast position, the same mammography unit, and the same electronic settings, but several months apart are obtained. Under ideal conditions, the second mammogram may be like the first mammogram, except for the appearance of a new growth or lesion. This ideal condition is illustrated in FIGS. 1 and 2. FIG. 1 shows an initial mammogram ("Mammo 0") at an initial time t=0 100. FIG. 2 is a mammographic image depicting an example of a subsequent mammogram ("Mammo T") at a later time t=T. Mammo T may be an example of the same breast tissue, when perfectly aligned with the tissue of the initial mammogram, showing the breast tissue and a model growth in the shape of "O" 102. In some embodiments, the absolute value of the difference between Mammo 0 and Mammo T is the growth O 102. This difference is shown in FIG. 3. This difference reveals the lesion, for example growth O 102, which grew in the interval 0≤t≤T.

One practical challenge includes placing the breast in exactly the same position to acquire Mammo 0 and Mammo T. Consequently, the growth of a lesion may often be obscured in the subtracted image, namely Mammo 0 minus Mammo T.

In one aspect of the subject technology, fiduciary markers, for example invisible tattoos, may be implanted in the breast to enable accurate repositioning of the breast, and consequently improve the subtraction of Mammo 0 from Mammo T. Experiments both with artificial breast models and in vivo may be implemented to establish the practical feasibility of the improved subtraction.

Various subtraction technologies may be implemented in conjunction with the subject technology. One aspect of the subject technology comprises a form of temporal subtraction radiography. Temporal subtraction radiography can be a form of digital mammography and may be defined as the subtraction of one radiographic image from a subsequent image. Temporal subtraction radiography may be useful in detecting radiographic changes, which have occurred during an intervening time interval. Temporal subtraction radiography may be easier to accomplish when the time interval between two sequential radiographs is small, e.g., a few seconds. With a longer intervening duration of time, non-identical patient positions add another dimension of a challenge to temporal subtraction.

Digital subtraction angiography (DSA) may be a form of temporal subtraction radiography. DSA may be accomplished by first taking a baseline digital radiograph (the mask) of a patient's anatomy and then immediately afterwards (with no movement of the patient) injecting radiopaque contrast agent in the patient's anatomy and taking additional radiographs of the patient's anatomy. When the patient does not move during the procedure, the anatomical structures seen in the mask radiograph can be subtracted from the subsequent images thereby providing exquisitely detailed results. Because the background anatomy is subtracted, the remaining contrast-enhanced vessels are revealed in amplified detail.

Digital subtraction may improve the sensitivity or accuracy of radiographs, for example chest x-rays, obtained at widely separated times. However, change in patient positioning, body size and shape over months or years results in misregistration of the radiographs and thus poor subtraction results. One approach may include use of software to align a patient's osseous landmarks (ribs and vertebrae) by means of non-linear warping of a radiographic image. After such a realignment and subtraction of two images, subtle pulmonary nodules should become more obvious.

The mammographic search for breast cancer calcifications is an unrealized potential application. Some embodiments of the subject technology utilize temporal subtraction radiography to improve or realize the potential for mammographic search for breast cancer calcifications. Some of the challenges encountered in mammography tests include the fact that the breast tissue is devoid of reliable radiographic anatomic landmarks. Other challenges include: 1) time intervals of a year or more between routine screening mammograms; 2) a lack of osseous anatomic landmarks, which would otherwise help align two asynchronous mammograms; and 3) the very small size of micro-calcifications associated with breast cancer. Some embodiments of the present technology may overcome at least some of these challenges.

In some embodiments of the subject technology, an architecture or apparatus and a procedure or method that uses the architecture to enhance the sensitivity and specificity or accuracy of detecting breast lesions obscured by fibroglandular tissue, for example, are described.

In some embodiments, one or more fiduciary markers, e.g., one or more tattoos, which may be invisible under normal circumstances, may be implanted in the breast to enable accurate repositioning of the breast. The one or more tattoos may be visible to the naked eye under ultra-violet light illumination or may be radiopaque. One or more methods or processes may be used to align and orient the breast between one or more positioning paddles of a mammography machine. For example, imaging software (e.g., non-linear warping) may be used to align two radiographic images of a breast.

One or more methods, architectures, or processes may be used to subtract an initial mammography or radiographic image at an initial time from a second mammography or radiographic image at a subsequent or later time. In some embodiments, enhancement software may be used to increase the sharpness or improve the accuracy of the subtracted image. In other embodiments, iterative geometric optimization and statistical inference, for example, may be used to repeatedly improve the matching of parts of objects that appear in both radiographic images. These processes can be done step-wise over separate sections of the mammogram or globally over the entire mammogram. The technique described herein can also be implemented in other applications such as mammographic tomosynthesis and forensic face recognition.

In general, the breast is placed between two pressure plates (e.g., Plate 1 and Plate 2), sometimes called paddle and platform. In some embodiments, one or more pressure plates are used for placing the breast. In other embodiments, the patient's breasts and the pressure plates can be modified to enable accurate subtraction of successive mammograms of the same breast.

FIGS. 4, 5 and 6 are exemplary images illustrating locations of pairs of opposing invisible tattoos 202 in a patient's breasts 200. In particular, FIG. 4 illustrates an example of a side view of tattoo locations for a craniocaudal (CC) view, for example, and FIG. 5 illustrates an example of a top view of tattoo locations for mediolateral oblique (MLO) view. FIG. 6 illustrates an example of a front view of tattoo locations for CC and MLO view. For clarification purposes, distinctive tattoo shapes have been used to distinguish tattoos adjacent to Plate 1 from tattoos adjacent to Plate 2. In FIGS. 4 to 6, triangular tattoos are placed adjacent to Plate 1, and star-shaped tattoos are placed adjacent to Plate 2. In some embodiments, one or more tattoos may be implemented for each view. In other embodiments, two or more tattoos may be implemented for each view. The technique described herein may be described as tattoo-aided subtraction radiography.

Figure 7:
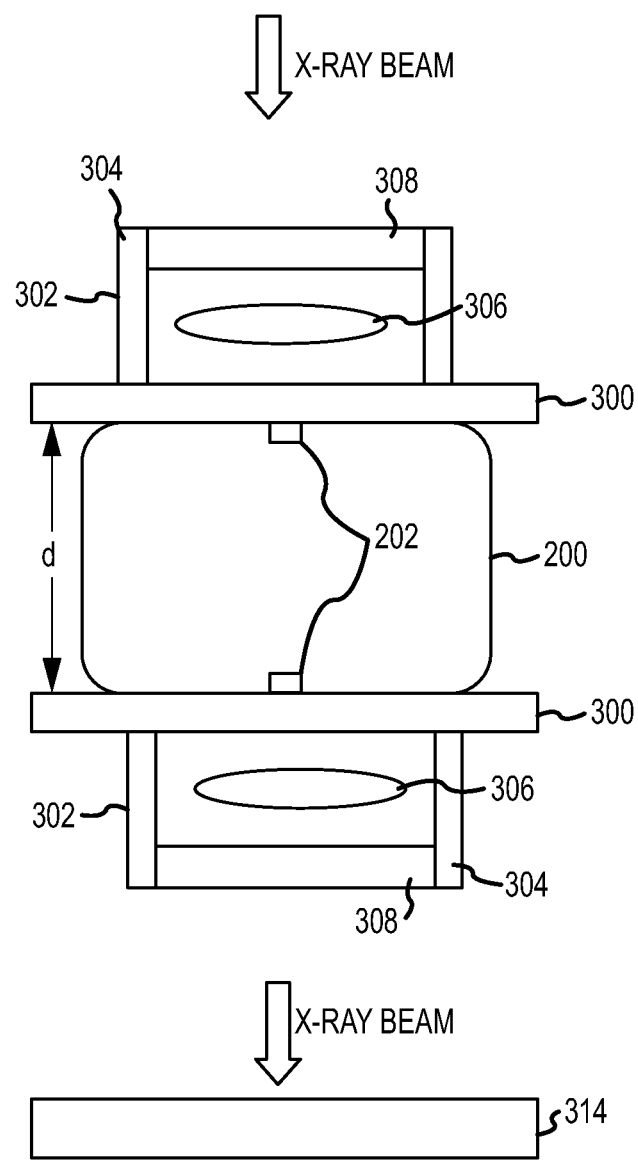
FIG. 7 is an example of a schematic representation of one aspect of an image acquisition architecture.

FIG. 7 is an example of a schematic representation of one aspect of an image acquisition architecture. In particular, FIG. 7 illustrates two tattoos 202 on opposite sides of a breast 200 placed between two pressure plates 300, as well as two removable cameras 302, including is some embodiments, an illuminator ring 304, lens 306, and high resolution image sensor 308, to help compute and control the positions of the two tattoos for mammographic imaging. In each camera, an image is detected and stored in an electronic sensor array.

One aspect of the subject technology, provides a way of determining the positions of the two tattoos in Mammo T (see, FIG. 2), and realigning the tattoos in Mammo T to match those in Mammo 0 (see, FIG. 1). The realignment may enable the display of abnormal growths by subtracting Mammo 0 from the realigned Mammo T.

Other embodiments of the subject technology enhance the visibility of abnormalities in breast imaging by improving the registration of successive mammograms. Repositioning the breast for two successive mammograms of the same breast may be carried out by controlling the following variables: d represents the distance between Plate 1 and Plate 2, (x1, y1) represents the position of the center of the tattoo image on Plate 1, and (x2, y2) represents the position of the center of the tattoo image on Plate 2.

In some embodiments, the process of repositioning the breast for two successive mammograms may include aligning the center of the axis of an x-ray beam so that it passes through the origins of the two image sensor arrays, $(x1, y1)=(x2, y2)=(0, 0)$, of Camera 1 and Camera 2. The process further can include, at time $t=0$, placing the patient's breast between the two Plates and measuring the value of d, denoted by $d(0)$, for example. The process also preferably includes, at time $t=0$, measuring and storing the positions of the two tattoos: $(x1(0), y1(0))$ and $(x2(0), y2(0))$. The vector displacement $(x2(0)-x1(0), y2(0)-y1(0))$ may be denoted by Q. An additional step is to obtain and store Mammo 0. In a further step of the process, Plate 1 is moved so that the tattoo of Mammo 0 at Plate 1 is imaged at the origin of the sensor array of Camera 1. Further, Plate 2 may be moved so that the tattoo of Mammo 0 at Plate 2 can be imaged at location Q in the sensor array of Camera 2.

In some embodiments, the process further includes, at time $t=T$, placing the patient breast between the two plates, setting $d(T)=d(0)$ and measuring and storing the position of the tattoo at Plate 1, i.e., $(x1(T), y1(T))$. In some embodiments, a further step of the process includes that Plate 2 can be moved in the xy domain so that $(x2(T), y2(T))=(x1(T), y1(T))+Q$, then obtaining and storing Mammo T. The process then, in some embodiments, continues to a further step, where Plate 1 can be moved so that the tattoo of Mammo T at Plate 1 can be imaged at the origin of the sensor array of Camera 1. The process also preferably includes moving Plate 2 so that the tattoo of Mammo T at Plate 2 is imaged at location Q in the sensor array of Camera 2.

In some embodiments, the process assures that the imaging optics for the tattoos are unchanged from Mammo 0 to Mammo T. In a further step of the process, a Gaussian filter may be used to suppress high-frequency noise in Mammo 0 and Mammo T. In some implementations, subcutaneous marks in combination with the nipple and the breast boundary can be used as a means of correcting small changes in gross shape of the breast in moving from one mammogram of a breast to a second mammogram of the same breast. In some embodiments, a correction for average density of the two images of the breast may be implemented (e.g., the correction may require that the two average densities are the same).

In some embodiments, some or all pixels or small blobs including densities equal to or exceeding those of typical microcalcifications are retained and the adjusted images are denoted as Mammo 0a and Mammo Ta. In another exemplary step, the process can include computing and storing |Mammo 0a−Mammo Ta|, i.e. the absolute value of the difference between Mammo 0a and Mammo Ta. In some embodiments, the subject technology enhances the visibility of abnormal growth in |Mammo 0a−Mammo Ta|.

Repositioning the breast, for example at a subsequent time, may produce non-uniform distortions because the breast is composed of soft tissue. The distortions may include distortions in a plane perpendicular to the x-ray axis such as translation and rotation distortion. Each of these types of distortions can appear in Plate 1 and Plate 2 in different amounts. In some implementations of the subject technology, additional tattoos can be used to overcome various combinations of these distortions. Translation distortion may be overcome, for example, by using two or more tattoos per image, as described above.

Figure 8:
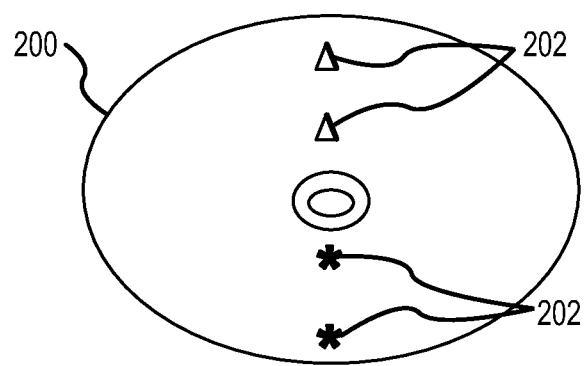
FIG. 8 is an example diagram illustrating a front view of four tattoos for a CC image.

For refinement of the subject technology, Plates 1 and 2 can be adjusted by translations and rotations in the xy plane. Plates 1 and 2 can also be adjusted by translations and rotations in the xyz plane or other rotational planes. Translation and rotation distortions may be suppressed by using four tattoos, for example, as illustrated in FIG. 8. In particular, FIG. 8 is an example diagram illustrating a front view of four tattoos 202 in a patient's breast 200 for a CC image.

Figure 9:
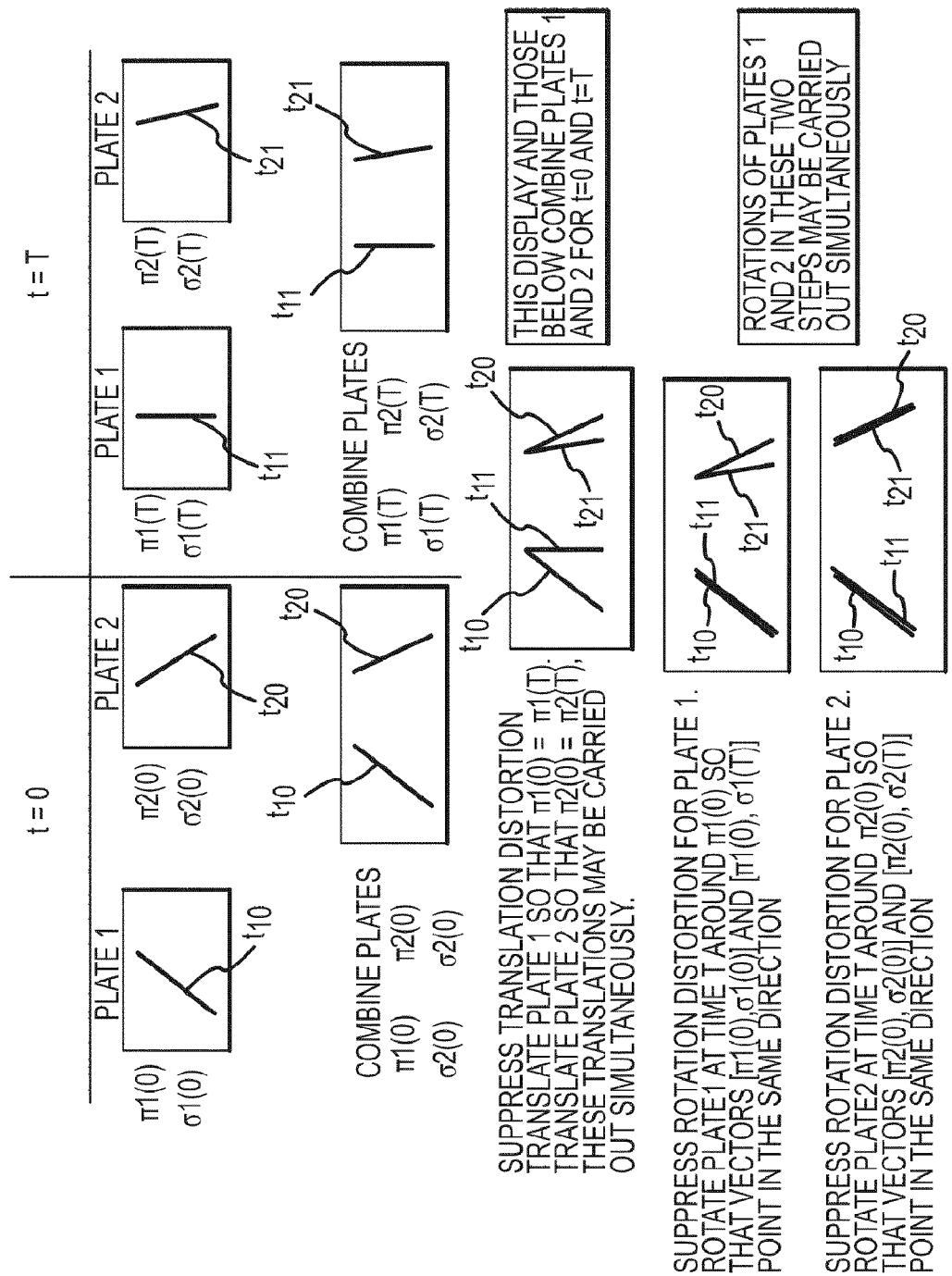
FIG. 9 illustrates an exemplary process for suppressing translation and rotation distortions using four tattoos per mammogram.

FIG. 9 illustrates an exemplary process for suppressing translation and rotation distortions using four tattoos per mammogram. Some aspects of the subject technology in include analysis of two CC views; one view at time $t=0$ and the other at time $t=T$. In some embodiments, each line segment of FIG. 9 joins a pair of tattoo images in the same Plate and each of the two Plates contributes its own distortion. The distortions associated with the two Plates may be separated in two parts: (i) distortions associated with Plate 1, and (ii) additional distortions associated with Plate 2.

In some embodiments of the subject technology, registration of distortions may be suppressed. An example of such suppression is illustrated with respect to FIG. 9, as follows. In FIG. 9, consider the top row of images of line segments. The $t_{10}$ line segment in this row joins two tattoos in Plate 1 at $t=0$, namely $\pi1(0)$ and $\sigma1(0)$. The $t_{11}$ line segment joins two tattoos in Plate 1 at $t=T$, namely $\pi1(T)$ and $\sigma1(T)$. The third row of images in FIG. 9 depicts the suppression of translation distortion in Plate 1 by translating Plate 1 at time T so that $\pi1(0)=\pi1(T)$. The outcome of this translation is depicted in the third row of FIG. 9 by translating the $t_{11}$ line segment until the upper endpoints of the $t_{10}$ and $t_{11}$ line segments coincide. In a similar manner, the outcome of the suppression of translation in Plate 2 is depicted in FIG. 9 by translating the $t_{21}$ line segment until the upper endpoints of the $t_{20}$ line segment and $t_{21}$ line segment coincide.

The fourth row of images in FIG. 9 shows the suppression of rotation distortion in Plate 1 by rotating Plate 1 around the upper endpoint of the $t_{10}$ line segment until the direction of the vector $[\pi1(T), \sigma1(T)]$ matches the direction of the vector $[\pi1(0), \sigma1(T)]$. This match is shown in FIG. 9 by the coincidence of the direction of the $t_{11}$ line segment with the direction of the $t_{10}$ line segment. The fifth row of images in FIG. 9 shows the suppression of rotation distortion in Plate 2 by rotating Plate 2 around the upper endpoint of the $t_{21}$ line segment until the direction of the $t_{21}$ vector $[\pi2(T), \sigma2(T)]$ matches the direction of the $t_{20}$ vector $[\pi2(0), \sigma2(0)]$. This match is shown in the fifth row of FIG. 9 by the coincidence of the direction of the $t_{21}$ line segment with the direction of the $t_{20}$ line segment.

In some embodiments of the subject technology, the registration distortions may include subcategories of registration distortions. Some examples of subcategories of translation are slide and roll, and some examples of subcategories of rotation are spin and twist. In some embodiments, two subcategories of registration distortion for translation, and two subcategories for rotation, may be visualized depending on whether the distortions in Plates 1 and 2 are equal or unequal. If the translation distortion in Plate 1 is equal to the translation distortion in Plate 2, the distortion may be equivalent to a rigid slide of the breast from one image formation to the next. If the translation distortions in Plate 1 and 2 are not equal, the distortions may be equivalent to a combination of a rigid slide and a nonrigid roll. In a roll, the skin of the breast rolls, or is moved about one or more axes between the plates, much like the motion of a chain tread wrapped around two wheels (as in a farm tractor, for example).

In some embodiments, if the rotation distortion in Plate 1 is exactly equal to the rotation distortion in Plate 2, the distortion may be equivalent to a rigid spin of the breast around an axis perpendicular to the x-ray beam or imaging x-ray. In some embodiments, the spin may be perpendicular to a line of sight of an imaging device for mammographic imaging. The spin can also be perpendicular to the xyz axis or some other axis of Plate 1 and/or Plate 2 and/or of the imaging device. If the rotation distortions in Plates 1 and 2 are not equal, the distortions are equivalent to a combination of a rigid spin and a nonrigid twist. In a twist, the skin of the breast adjacent to Plate 1 and the skin of the breast adjacent to Plate 2 are rotated in opposite directions (clockwise and counter clockwise, for example).

In some embodiments of the subject technology, more than four tattoos per image may be used to overcome complex geometric transformations in successive imaging of the same breast as illustrated in FIGS. 10 to 12. In the embodiments illustrated in FIGS. 10 to 12, the breast includes twelve tattoos: six tattoos next to an upper plate, and six tattoos next to a lower plate. In particular, FIG. 10 illustrates an example of a breast 200 compressed between two plates 300 translucent to ultraviolet light. Each tattoo may be configured to fluoresce under ultraviolet illumination. In some embodiments, the upper six tattoos 202 may be arranged in three pairs and each pair may be oriented perpendicular to the nipple-chest axis. The lower six tattoos 202 may be oriented in three pairs and each pair may be oriented parallel to the nipple-chest axis. In some embodiments, the number of tattoos may be more than six or less than six. For example, the number of tattoos can be 1, 2, 3, 4, 5, 7, 8 or more, on one or both sides of the breast. In some embodiments, a single tattoo can be used that has the specific design that accomplishes the same purpose as multiple tattoos.

Ultraviolet light illumination and a flexible plastic alignment tool 310 shown in FIG. 11 may assist in the precise alignment of the breast. FIG. 12 shows how the superposed x-ray images of the upper and lower arrays of tattoos 202 can help achieve precise positioning of the breast in preparation of subtraction of two temporally separated mammograms. Before subtracting the two temporally spaced mammograms, a user, e.g., a radiologist, may adjust the two compression plates, or paddles, so that fibroglandular tissue in the two mammograms precisely overlaps. In some embodiments of the subject technology, multiple tattoos may be used to overcome complex geometric distortions in successive imaging of the same breast. In addition, iterative adaptive procedures may be used to suppress the additional distortions revealed by the multiple tattoos.

Figure 13:
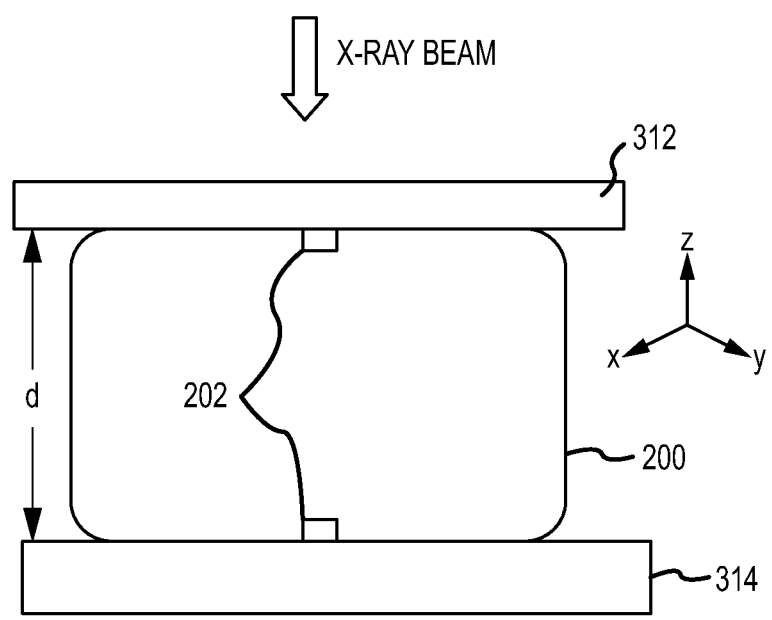
FIG. 13 illustrates an example of a simplified tattoo-based registration architecture or system.

Referring to FIG. 13, an example of a simplified tattoo-based registration architecture or system is illustrated. In some embodiments of the simplified tattoo-based registration architecture or system, the visible-light cameras are eliminated, and registration distortions are corrected with the aid of x-ray imaging. In some embodiments of the simplified tattoo-based registration architecture or system, the paddle may be adjusted in the xy plane such that the relative positions of the two tattoos 202 in a breast 200 at time t=T are identical to their relative positions at t=0. The paddle may be referred to as a xy-adjustable paddle 312. One example of an adjustable paddle is a Hologic "contact paddle" 314 illustrated in FIG. 14.

Some embodiments of the subject technology use invisible tattoos on a breast as permanent references for accurate repositioning of the breast. The invisible tattoos may be configured to enable enhancement of visibilities of abnormal growths after subtraction of successive mammograms. The tattoos may be based on a modification of a technique described in Richard R. Anderson, et al., Permanent, removable tissue markings, U.S. Pat. No. 6,814,760 ("Richard"), incorporated by reference herein. Richard describes a "removable tattoo ink" comprising micro particles with a capsule containing water soluble colored ink. The microparticles can be made in many different non-toxic colors and injected into the dermis to create a permanent visible but removable decorative tattoo. Some aspects of the subject technology use microparticles that create permanent, minimally diffusible, invisible radiopaque or fluorescent tattoos. The capsule can be designed so that when a specific wave length of intense light (e.g., a laser) is focused on the tattoo, the capsule ruptures, releasing the pigment that is then absorbed systemically and excreted. Thus, the proposed tattoos can be removed without scarring if requested by the patient.

Figure 14:
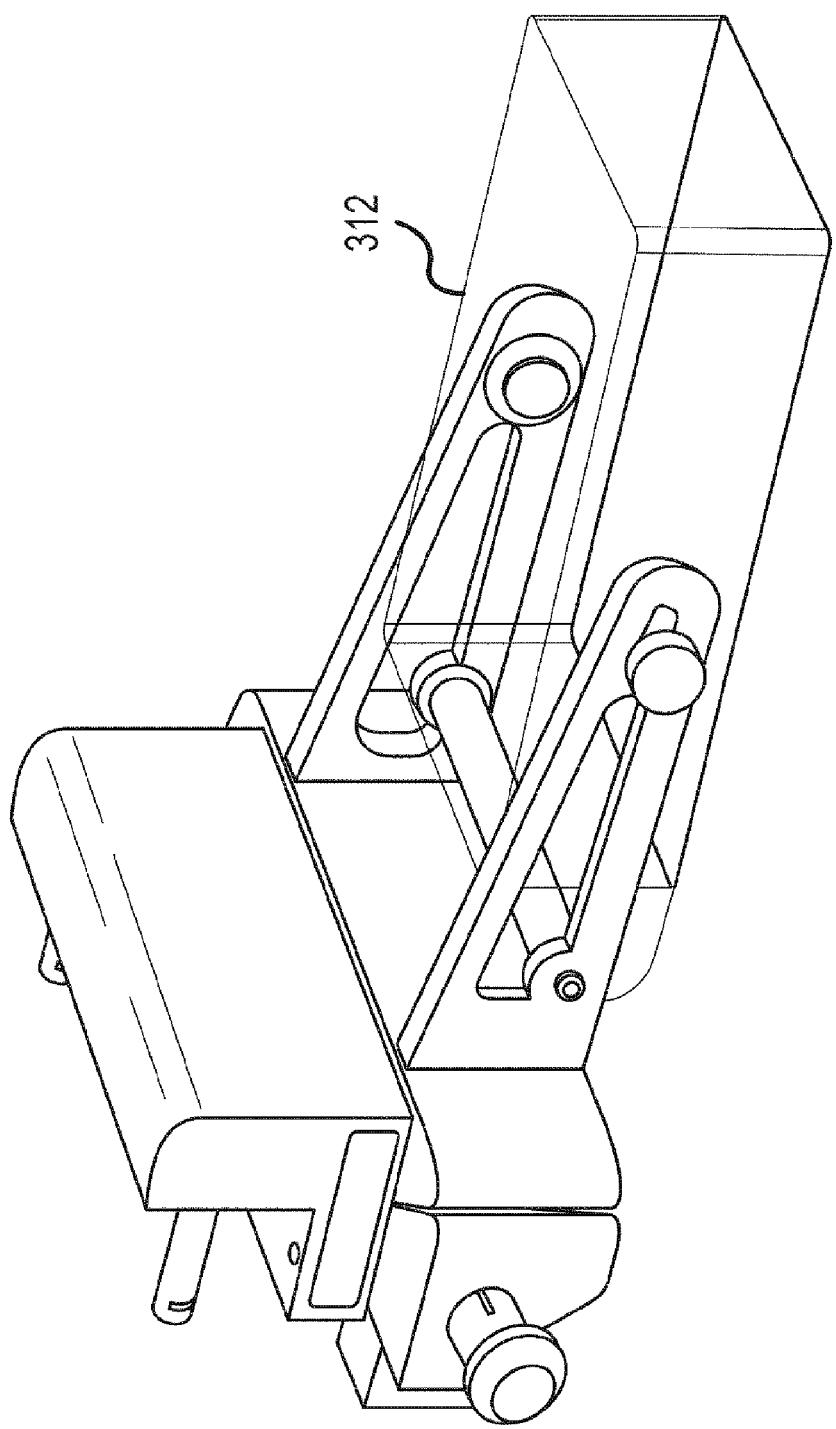
FIG. 14 illustrates an example of an xy-adjustable paddle.
Figure 15:
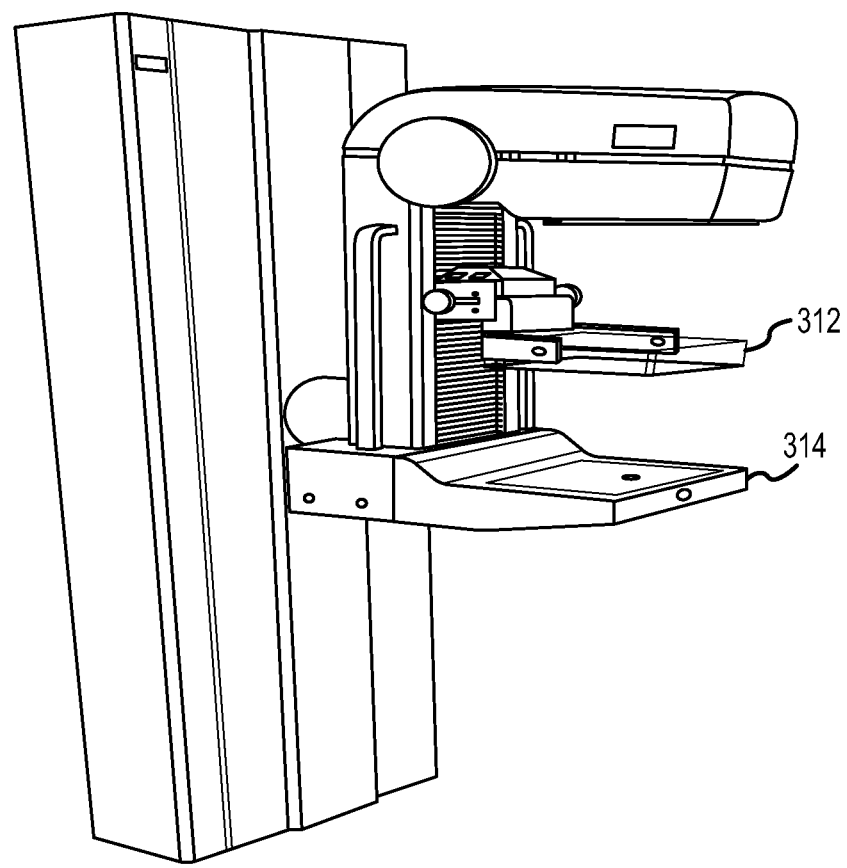
FIG. 15 illustrates an example of a mammography unit.
Figure 16:
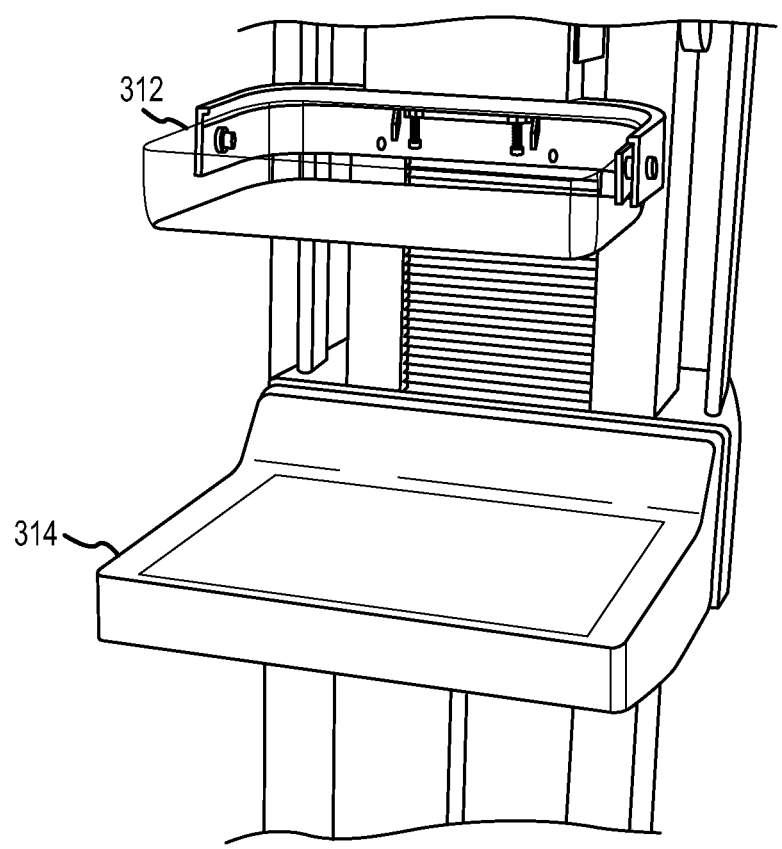
FIG. 16 illustrates an example of a transparent paddle and sensor platform.
Figure 17:
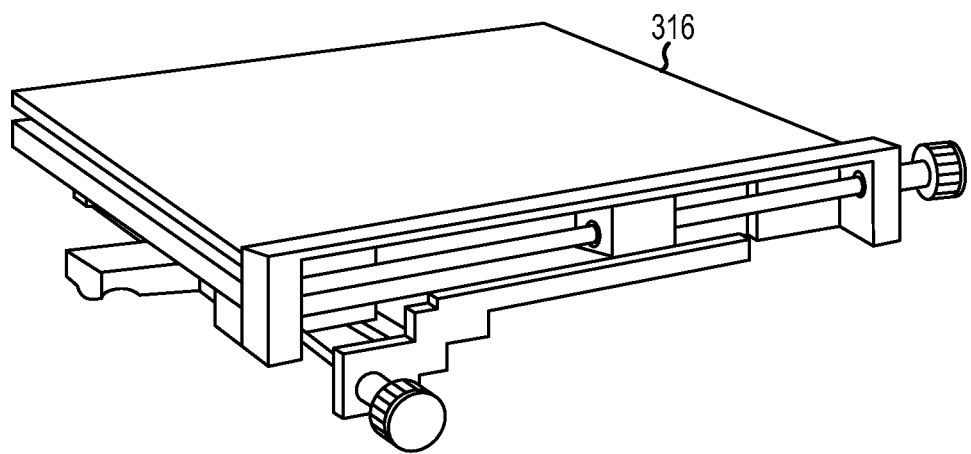
FIG. 17 illustrates an example positioning microscope stage.

The feasibility of some aspects of the subject technology may be tested or verified using different physical models. One example of a physical model comprises a digital mammography unit, e.g., Hologic Selenia Full Field Digital Mammography Unit, positioning microscopic stage, e.g., a Modified adjustable Hologic Selenia Contact Paddle or Semprex Corporation manual fine positioning microscope stage, and a radiological breast phantom, e.g., California Medical Innovations radiological breast phantom. The radiological breast phantom may be a fabricated custom breast phantom that simulates the flexibility and softness of human breast. The Hologic Selenia Mammography Unit is illustrated in FIG. 15. A close-up of the paddle 312 and the sensor platform 314 is shown in FIG. 16. Some embodiments include a fine-positioning microscope stage 316, as shown in FIG. 17. One example of a microscope is made by Semprex®. The positioning microscope stage may comprise a 6.5-inch by 6.5-inch glass window, which may be transparent to x-rays. This microscope stage can be attached firmly to a frame of the mammography unit. In some embodiments, a suitable attachment device may be constructed for the microscope unit or microscope stage. In other embodiments, an alternative to the microscope stage may be constructed by modifying a contact paddle manufactured by Hologic™, for example, for use on a mammography unit such as the Hologic Selenia Mammography Unit. An example of such a paddle 312 is illustrated in FIG. 14. The paddle may be modified to make it adjustable in units of 0.1 mm in a horizontal plane.

The following experiment may be carried out on the breast phantom to demonstrate the effectiveness, in conjunction with the phantom, of embodiments of the subject technology, using the four tattoo arrangement of FIG. 8. The four tattoos can be identified by a name, e.g., TAT1, TAT2, TAT3, and TAT4. At t=0 an x-ray image may be produced of the breast phantom. In the x-ray image, the vector positions of all of the tattoos may be measured as described above with reference to FIG. 7 and the following description of detection enhancement. In the x-ray image, each of the tattoos may be marked by their names. The tattooed breast phantom can then be removed and manually placed in the paddle close to the position at t=0. At t=T, a second x-ray image of the breast phantom may be produced. Similar to the preceding image, each of the tattoos may be marked by their names.

The marked x-ray images at t=0 and t=T, may be referred to as M0 and MT, respectively. Comparing M0 and MT, Plate 1 may be adjusted to produce a third Image MT' so that the marked tattoos in MT' coincide with those in M0. The microcalcifications in successive images can also be matched. The tattoos and microcalcifications may be referred to as critical points. The mechanical method sketched in FIG. 9 can serve as a guide for this process, but manual identification may also supplement this process. Matching of the noncritical points in M0 and MT may be carried out by iterative geometric optimization—a form of machine learning. For further information on iterative geometric optimization techniques, see Richard O. Duda, et al., *Pattern Classification*, Second Edition, John Wiley & Sons, New York, 2001, Section 10.8, pp. 548-550 and Kenichi Kanatani, Yasuyuki Sugaya, "Performance evaluation of iterative geometric fitting algorithms," *Computational Statistics & Data Analysis*, Volume 52, Issue 2, October 2007, pp. 1208-1222, incorporated by reference herein.

The following includes a description of an exemplary iterative geometric optimization for registering successive radiographic images (i.e., mammograms) of a phantom breast or a breast in vivo. The breast or phantom may be marked by punctate tattoos, and the successive images may undergo complex nonlinear transformations. The breast or phantom may be modeled as an inflatable and deflatable balloon covered by a uniformly spaced layer of pixels (i.e., a digital "skin"). When the breast is compressed by two parallel paddles, the pixels of the digital skin contacted by each paddle form rectangular arrays.

Figure 21:
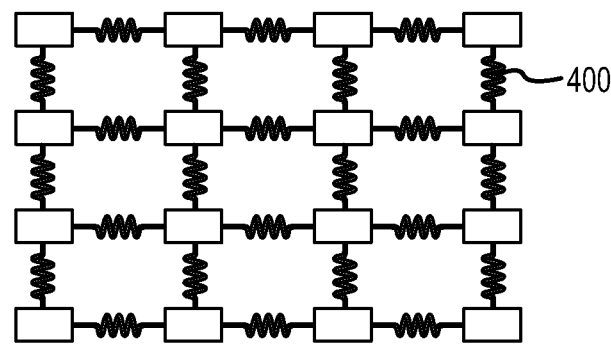
FIG. 21 is an exemplary illustration of horizontally or vertically spaced pair of pixels tied by a computer-simulated nonlinear spring.
Figure 22:
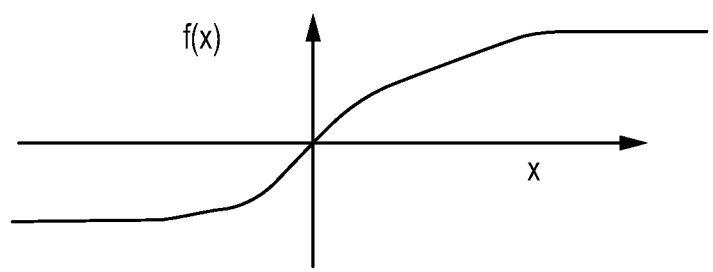
FIG. 22 is an example plot of a monotonic nonlinear function f(x) that represents the character of the computer-simulated nonlinear springs.

In some embodiments, every pair of vertically or horizontally adjacent pixels in this array is spaced 100 μm (0.1 mm) apart, which is small enough to resolve most mammographic microcalcifications. Each horizontally or vertically spaced pair of pixels may be tied by a nonlinear spring 400, as illustrated in FIG. 21. These springs can simulate the elastic warping of the digital skin produced by changes in position of the breast or breast phantom between the paddles from time 0 to time T. Each spring can be characterized by a monotonic nonlinear function f(x), where x denotes tension (pull) or compression (push), and f(x) denotes extension or shortening of the spring. The function f(x) may or may not be symmetric with respect to the origin. FIG. 22 shows an example of f(x). Each box in this array stores a measure of the brightness of the mammogram at the pixel's location. Some of the pixels are marked by distinctively recognizable punctated tattoos.

When two successive mammograms are produced, subtraction of the two mammograms may be implemented by subtracting the brightness of corresponding pixels. The corresponding pixels may be found by matching the corresponding tattoos by a sequence of transformations. In transformation 1, for example, mechanical translations and rotations of the two paddles are implemented at time T, as illustrated in the description with respect to FIG. 9. In transformation 2, for example, software inflation or deflation of an abstract balloon, may account for a possible increase or decrease in the size of the breast from time 0 to time T. In transformation 3, for example, software warping of the digital skin may account for the remaining mismatches among the tattoos. The result of this transformation or step may achieve a match of all tattoos, but may also leave some mismatches of pixels between the tattoos.

Figure 23:
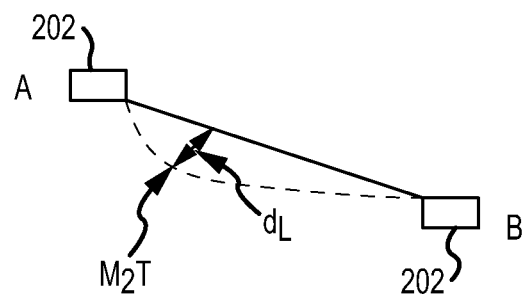
FIG. 23 illustrates an example comparison of the pixel values along the solid straight line from Tattoo A to Tattoo B in image M0 and along the transformation of the line in image MT after completion of transformation 3.

FIG. 23 shows a possible mismatch of a straight line between two tattoos 202 at time 0, and the transformed arc at time T (dashed curve) after the completion of transformation 3. In transformation 4, for example, software warping of the digital skin may minimize the mismatches of pixels between the tattoos. This warping process can be a nonlinear transformation guided by the digital skin model represented in FIG. 21. In some embodiments, an iterative geometric optimization is used to minimize the mismatches of non-tattoo pixels.

In some embodiments of iterative geometric optimization, a vector of parameters w may be constructed that represents the elastic warping produced by the digital skin. Each value of w can represent the nonlinear warping provided by the springs of the digital skin. An example of w may be the vector $[w_0\ w_1\ w_2\ w_3\ w_4\ w_5]$, where $w_i$ are the parameters in a polynomial representing the force-displacement relation of the springs. Therefore the function f(x) may comprise:

$$f(x) = w_0 + w_1 + w_2 + w_3 + w_4 + w_5.$$

In some embodiments, the deviations of the pixel values in image MT from the corresponding pixels in image M0 may be estimated for each value of w. Referring to FIG. 23, a comparison of the pixel values along the solid straight line from Tattoo A 202 to Tattoo B 202 in image M0 and along the transformation of this line in image MT after completion of TR3 is illustrated.

In some embodiments, $d_1$ denotes an integrated difference between the two series of pixel values. In some embodiments, w may be changed to produce another arc joining Tattoo A to Tattoo B in image MT. In some embodiments, following the concepts of statistical inference, statistical variations in w may be introduced to improve the quality of the search for an optimum value of w. Each candidate w may produce a candidate arc joining the two tattoos. The dashed curve of FIG. 23 is an example of such an arc. The difference between the pixels on the straight arc in image M0 to the pixels along the dashed curve in image MT may be computed and denoted by $d_2$. Continuing in this manner can result in a valley in w space, generating the depth of the valley $d_i$ (or the deviation of the dashed curve from the straight line), to achieve best warping of the skin between tattoos while maintaining the matching of the tattoos in M0 and MT. The value of w at the lowest depth $d_L$ may be denoted by $w_L$ and the geometrically optimized image at time T achieved by $w_L$ may be denoted by $M_L T$. Subtracting $M_L T$ from M0, can produce the image $D_L(0,T)$. In some embodiments, if MT contains small growths such as microcalcifications formed after time 0, the image $D_L(0,T)$ can reveal those growths and suppress the fibroglandular tissue.

Figure 24:
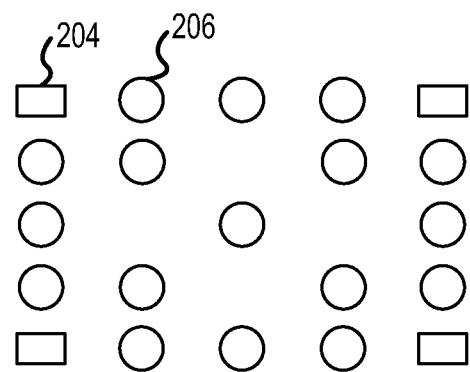
FIG. 24 is an exemplary diagram illustrating tattoos used for modeling the positions of unmatched pixels in addition to the tattoos used for matching pixels to facilitate modeling of the warping of the breast in the digital skin.

To facilitate modeling of the warping of the breast in the digital skin, tattoos may be used for modeling the positions of unmatched pixels in addition to the tattoos used for matching pixels. An example of this concept is illustrated in FIG. 24 where the squares denote tattoos 204 for matching and the circles denote tattoos 206 for modeling. The above described techniques can perform mammographic screening with greater sensitivity and specificity.

Figure 25:
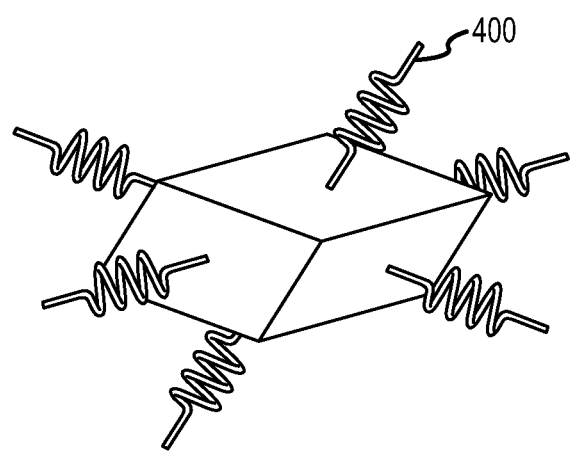
FIG. 25 illustrates an example of a computer-simulated spring loaded three dimensional pixel.

Referring to FIG. 25, exemplary spring-loaded 400 three-dimensional (3D) pixels are illustrated. The fiduciary markers, for example invisible tattoos, can enhance the medical utility of 3D mammography and 3D pulmonary radiography. Some examples of 3D mammography can be provided or generated by computer tomography (CT) and tomosynthesis. The application of techniques described herein, e.g., tattoo-aided subtraction radiography, to CT mammography and CT pulmonary radiography enhances the sensitivity and specificity of screening for breast cancer and lung cancer, for example. In some embodiments of 3D applications of tattoo aided subtraction radiography, the tattoos are implanted on the skin of the breast or chest to surround the 3D search region. The use of CT for mammography, benefits from the elimination of paddles to compress the breast. In some embodiments, the process of registering and subtracting two temporarily spaced radiographs may comprise storing each of the two radiographs on a 3D network of spring-loaded 3D pixels such as those illustrated in FIG. 25. The process further comprises superimposing the two radiographs so that the corresponding tattoos match. The process further comprises matching nearby pixels, starting at each tattoo, to minimize the summed differences of subtracted contents of the matched pixels. This technique may require a geometric iterative optimization similar to the iterative optimization described herein.

In some embodiments, some residual distortions may remain after realigning opposing tattoos. These residual distortions may be suppressed by off-line post-processing. Examples of such residual distortions include layered shift and layered spin. Consider a breast consisting of thin planar layers parallel to the two compression plates, each layer containing no more than one calcification. After realigning the opposing tattoos of the breast at time t=T to the same relative positions as at time t=0, the positions of the planar layers at time t=T may have moved from their positions at time t=0, resulting in residual distortions.

Figure 18:
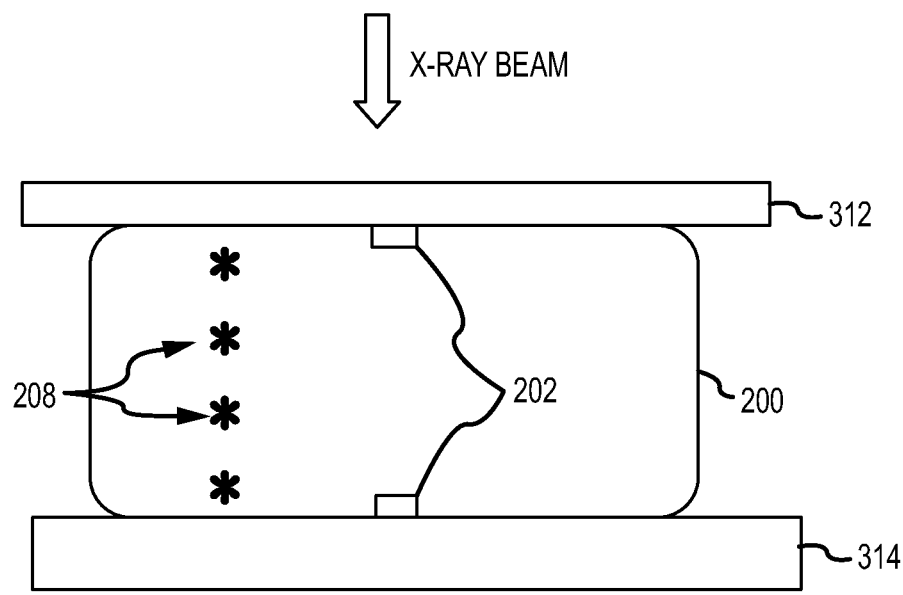
FIG. 18 illustrates an example of a compressed artificial spherical model of breast tissue with opposing tattoos aligned vertically along the x-ray beam.
Figure 19:
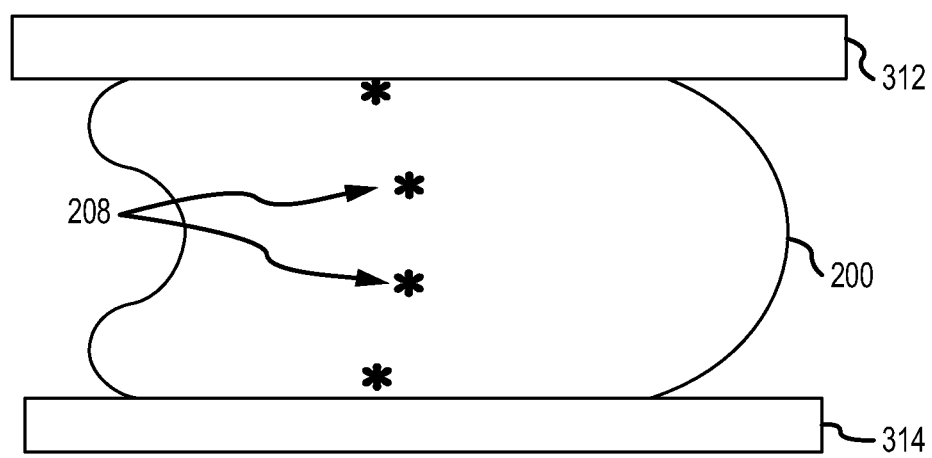
FIG. 19 illustrates a front view of a compressed breast with planar layers containing two calcifications shifted to the right.

Referring to FIG. 18, an example of a compressed artificial spherical model of breast tissue 200 with opposing tattoos 202 aligned vertically along the x-ray beam is illustrated. Four microcalcifications 208 are shown in a vertical alignment. Referring to FIG. 19, a front view of the same compressed breast 200 is shown, but with the planar layers containing two calcifications 208 shifted to the right, thereby shifting two of the calcifications to the right. Note the resulting distortions of the two vertical breast boundaries in this view. The shifted calcifications are examples of a layered shift residual distortion.

Figure 20:
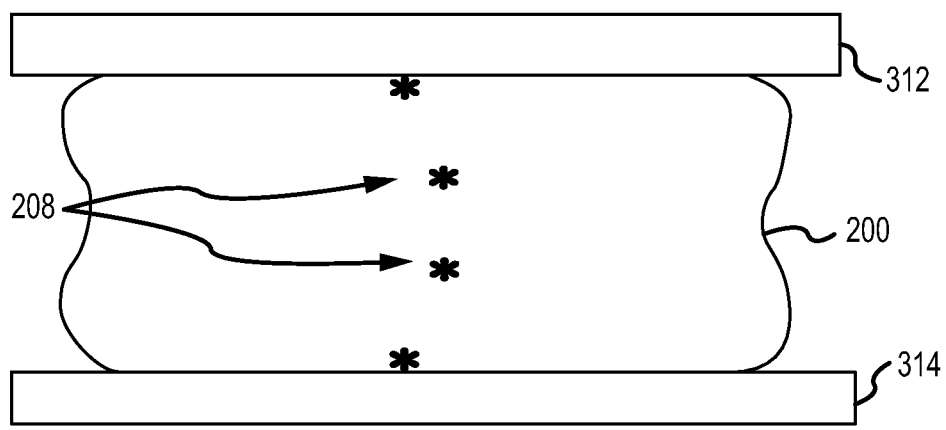
FIG. 20 illustrates examples of distorted locations of the two intermediate calcifications, and a narrowing of the intermediate diameter of the breast.

In some embodiments, layered spin residual distortion can be explained by returning to the embodiments depicted in FIG. 18, an illustration of a compressed breast 200, with the tattoos 202 aligned, and no residual distortion. Two planar layers, each containing the one of the two intermediate calcifications 208, can be defined between the top and bottom calcifications. These planar layers are referred to as "intermediate." These intermediate layers can be rotated a few degrees around the axis through the centers of the two opposing tattoos. The resulting front view, shown in FIG. 20, reveals distorted locations of the two intermediate calcifications 208, and a narrowing of the intermediate diameter of the breast 200.

The foregoing description is provided to enable a person skilled in the art to practice the various embodiments described herein. While the present subject technology has been particularly described with reference to the various figures and embodiments, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these embodiments will be readily apparent to those skilled in the art, and generic principles defined herein may be applied to other embodiments. Thus, many changes and modifications may be made to the subject technology, by one having ordinary skill in the art, without departing from the scope of the subject technology.

A phrase such as "an aspect" does not imply that such aspect is essential to the subject technology or that such aspect applies to all embodiments of the subject technology. A disclosure relating to an aspect may apply to all embodiments, or one or more embodiments. An aspect may provide one or more examples. A phrase such as an aspect may refer to one or more aspects and vice versa. A phrase such as "embodiments" does not imply that such configuration is essential to the subject technology or that such configuration applies to all embodiments of the subject technology. A disclosure relating to a configuration may apply to all embodiments, or one or more embodiments. A configuration may provide one or more examples. A phrase such as "configuration" may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

A reference to an element in the singular is not intended to mean "one and only one" unless specifically stated, but rather "one or more." The term "some" refers to one or more. All structural and functional equivalents to the elements of the various embodiments described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the claims. Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A system for imaging a portion of a subject's body, comprising:
    a first contact member configured to contact a first side of the portion;
    a second contact member configured to contact a second side of the portion substantially opposite the first side;
    a first image sensor, coupled to the first contact member and configured to detect a position of a first fiducial marker located at the first side;
    a second image sensor, coupled to the second contact member and configured to detect a position of a second fiducial marker located at the second side; and
    an alignment system that receives information from at least one of the first or second image sensors and, based on the information, moves at least one of the first or second contact members such that the portion moves and the positions of the first and second fiducial markers become aligned.

2. The system of claim 1, further comprising the first fiducial marker, wherein the first fiducial marker is configured to be placed within about 1 cm of a skin surface at the first side.

3. The system of claim 2, further comprising the second fiducial marker, wherein the second fiducial marker is configured to be placed within about 1 cm of a skin surface at the second side.

4. The system of claim 1, wherein the first contact member comprises a paddle.

5. The system of claim 1, wherein the first and second fiducial markers each comprises one or more tattoos.

6. The system of claim 1, wherein the first and second fiducial markers are not visible to the unaided human eye.

7. The system of claim 1, wherein the first and second fiducial markers are visible to the unaided human eye when subject to ultraviolet illumination.

8. The system of claim 1, wherein the first and second fiducial markers are radiopaque.

9. The system of claim 1, wherein the alignment system comprises imaging software configured to further facilitate alignment of the first and second fiducial markers.

10. The system of claim 1, further comprising an electromagnetic radiation system to generate electromagnetic radiation to facilitate generation of an image of the portion.

11. The system of claim 10, wherein the electromagnetic radiation comprises x-rays.

12. The system of claim 10, further comprising at least a first radiographic image acquisition platform configured to acquire a first radiographic image of the portion.

13. The system of claim 12, further comprising a subtraction imaging system configured to subtract the first image from the second image to facilitate detection of changes in the portion that have occurred over time.

14. The system of claim 1, wherein the first and second image sensors are configured to detect the respective positions of the first and second fiducial markers, wherein at least one of the first or second fiducial markers is implanted in the portion.

15. A system for imaging a portion of a subject's body, comprising:
    a first imaging member having a first image sensor configured to detect a position of a first fiducial marker located at a first side of the portion;
    a second member having a second image sensor configured to detect a position of a second fiducial marker located at the second side of the portion, the second side being substantially opposite the first side; and
    an alignment system that receives information from at least one of the first or second image sensors and, based on the information, moves at least one of the first or second members such that the portion moves and the positions of the first and second fiducial markers become aligned.

16. A method for imaging a portion of a subject's body, comprising:
    contacting a first side of the portion with a first contact member;
    contacting a second side of the portion substantially opposite the first side with a second contact member;
    detecting a position of a first fiducial marker located at the first side with a first image sensor, coupled to the first contact member;
    detecting a position of a second fiducial marker located at the second side with a second image sensor, coupled to the second contact member;
    acquiring information at an alignment system from at least one of the first or second image sensors; and
    based on the acquired information, moving at least one of the first or second contact members such that the portion moves and the positions of the first and second fiducial markers become aligned.

17. The method of claim 16, wherein the moving comprises moving at least one of the first and second contact members such that the portion is moved to align the fiducial markers based on the information received.

18. The method of claim 17, wherein the moving comprises contacting the portion on the first side with the first member and on the second side with the second contact member.

19. The method of claim 16, further comprising placing the first fiducial marker within about 1 cm of a skin surface at the first side.

20. The method of claim 19, further comprising placing the second fiducial marker within about 1 cm of a skin surface at the second side.

21. The method of claim 16, further comprising aligning the first and second fiducial markers using imaging software.

22. The method of claim 16, further comprising generating electromagnetic radiation to generate a radiographic image of the portion.

23. The method of claim 16, wherein the moving comprises moving at least one of the first or second contact members such that the portion moves and the positions of the first and second fiducial markers become superimposed.

* * * * *